United States Patent [19]

Fäh et al.

[11] 4,332,811
[45] Jun. 1, 1982

[54] 1,3-BENZODITHIOL-2-N,N-DIALK-YLIMINIUM SALTS AND PESTICIDAL USE

[75] Inventors: Hansjakob Fäh, Ormalingen; Saleem Farooq, Ettingen; Alfred Grieder, Böckten; Karl Scheuzger, Basel, all of Switzerland

[73] Assignee: Ciba-Geigy Corporation, Ardsley, N.Y.

[21] Appl. No.: 246,352

[22] Filed: Mar. 23, 1981

[30] Foreign Application Priority Data

Mar. 26, 1980 [CH]  Switzerland .......................... 2373/80
Sep. 16, 1980 [CH]  Switzerland .......................... 6930/80

[51] Int. Cl.³ .................... A01N 43/28; A01N 43/40; C07D 339/06; C07D 409/04
[52] U.S. Cl. .................................. 424/267; 424/274; 424/277; 546/197; 549/32; 548/526
[58] Field of Search ............... 260/326.5 SA, 326.84; 546/197; 549/32; 424/267, 274, 277

[56] References Cited

U.S. PATENT DOCUMENTS 4,287,204  9/1981  Farooq ............................. 424/277

*Primary Examiner*—Richard Raymond
*Attorney, Agent, or Firm*—Frederick H. Rabin; John P. Spitals

[57] ABSTRACT

Novel substituted 1,3-benzodithiol-2-N,N-dialkyliminium salts of the formula

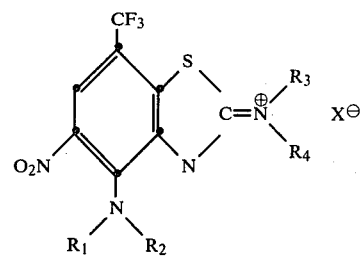

wherein $R_1$ and $R_2$ independently of one another are each hydrogen, $C_1$–$C_5$-alkyl, $C_3$–$C_6$-cycloalkyl, $C_3$-alkenyl, $C_3$–$C_5$-alkynyl or the radical —$(CH_2)_n$—OR, in which R is $C_1$–$C_4$-alkyl, and n is the number 2 or 3; $R_3$ and $R_4$ independently of one another are each $C_1$–$C_4$-alkyl, or together they are the radical —$(CH_2)_4$— or —$(CH_2)_5$—; and $X^\ominus$ is a molar equivalent of an anion of an inorganic or organic acid; processes for producing these compounds, as well as compositions containing them, and their use for combating pests, particularly for combating members of the order Acarina which infest plants and animals. The novel compounds are distinguished by their special effectiveness against mites which damage plants.

10 Claims, No Drawings

1,3-BENZODITHIOL-2-N,N-DIALKYLIMINIUM SALTS AND PESTICIDAL USE

The present invention relates to novel substituted 1,3-benzodithiol-2-N,N-dialkyliminium salts, to processes for producing them, and to their use for combating pests.

The novel iminium salts according to the invention have the formula I

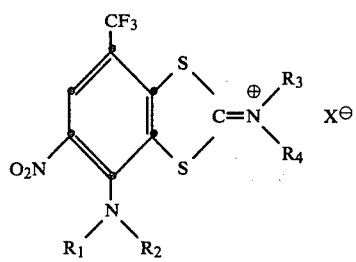

wherein $R_1$ and $R_2$ independently of one another are each hydrogen, $C_1$–$C_5$-alkyl, preferably $C_1$–$C_4$-alkyl, $C_3$–$C_6$-cycloalkyl, $C_3$-alkenyl, $C_3$–$C_5$-alkynyl or the radical —$(CH_2)_n$—OR, in which R is $C_1$–$C_4$-alkyl, and n is the number 2 or 3, $R_3$ and $R_4$ independently of one another are each $C_1$–$C_4$-alkyl, or together they are the radical —$(CH_2)_4$— or —$(CH_2)_5$—, and $X^\ominus$ is a molar equivalent of an anion of an inorganic or organic acid.

Compounds of the formula I according to the invention which are of particular interest are those wherein $R_1$ and $R_2$ independently of one another are each hydrogen, $C_1$–$C_4$-alkyl, $C_3$-alkenyl, $C_3$-alkynyl or 2-methoxyethyl, and $R_3$ and $R_4$ are methyl. Compounds of the formula I preferred on account of their activity as pesticidal active substances are also those wherein $R_1$ is hydrogen. Valuable compounds by virtue of their biological effectiveness are also compounds of the formula I wherein the anion $X^\ominus$ is chloride, bromide, iodide, sulfate, hydrogen sulfate, chlorate, perchlorate, rhodanide, nitrate, phosphate, hydrogen phosphate, tetrafluoroborate, acetate, trichloroacetate, trifluoroacetate, phenylsulfonate, oxalate, malonate, succinate, malate, tartrate or citrate, preferably however perchlorate, hydrogen sulfate, iodide or rhodanide.

From the German Offenlegungsschrift No. 2,644,036 are known already 1,3-benzodithiol-2-one and 1,3-benzodithiol-2-thione compounds which are described therein as being herbicidally, fungicidally, acaricidally, nematocidally and insecticidally effective. Reference is made in J. Org. Chem. 44/2, 267 ff (1979) to the production of 4-nitro-6-trifluoromethyl-1,3-benzodithiol-2-N-alkylimines. Quaternary iminium salts of 2-alkyliminonaphtho[2,3]-1,3-dithiol-4,9-diones and production processes therefor are known from J. Am. Chem. Soc. 73, 3460 (1951).

It has now been found that surprisingly the compounds of the formula I according to the invention, whilst having high tolerance to plants and negligible toxicity to warm-blooded animals, have an excellent degree of effectiveness as pesticidal active substances, particularly as active substances for combating members of the order Acarina which infest plants and animals. The compounds of the formula I are suitable in particular for combating members of the order Acarina of the families: Ixodidae, Argasidae, Tetranychidae and Dermanyssidae, as well as for combating insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. Also surprising is that compounds of the formula I exhibit a marked leaf-penetration effect, which renders them suitable especially for combating species of pests that settle on the underside of the leaves of infested plants.

By virtue of their good acaricidal effectiveness, the compounds of the formula I are suitable also for combating ectoparasites in both domestic and productive animals, for example by treatment of animals, livestock housing and pasture land.

To be particularly emphasised is that the compounds of the formula I have a surprisingly intense and specific action against mites which damage plants, and against zooparasitic mites. The compounds of the formula I can thus be used for combating phytophagous mites, for example of the families: Tetranychidae and Phytoptipalpidae (spider mites), Tarsonemidae (soft-bodied mites) and Eriophyidae (gall mites). The compounds of the formula I are suitable for combating in particular the following genera of mites which infest fruit and vegetable crops: *Tetranychus urticae, Tetranychus cinnabarinus, Panonychus ulmi, Bryobia rubrioculus, Panonychus citri, Eriophyes pyri, Eriophyes ribis, Eriophyes vitis, Tarsomemus pallidus, Phyllocoptes vitis* and *Phyllocopt-ruta oleivora*. It is possible with the aid of compounds of the formula I to also combat zooparasitic mites, for example of the families: Sarcoptidae, Psoroptidae, Dermanyssidae and Demodicidae, especially mange mites of the genera *Sarcoptes scabiei* and *Notoedres cati*, which bore their way deeply into the epidermis of the infested domestic and productive animals as far as the nerve ends and cause intense irritation and damage in the animals; also the genera *Dermanyssus gallinae* and *Psoroptes ovis* can be combated by the compounds of the formula I.

The novel iminium salts of the formula I are produced according to the invention by reacting a 2-nitrophenyl-N,N-dialkyldithiocarbamate of the formula II

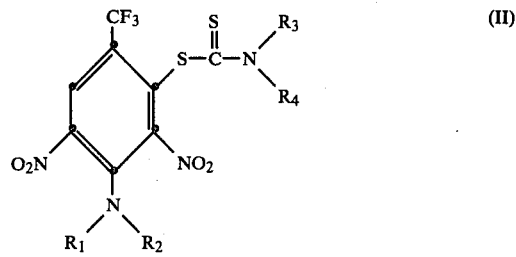

wherein $R_1$, $R_2$, $R_3$ and $R_4$ have the meanings defined under the formula I, in the presence of an inert solvent, with a preferably strong acid of the formula III $$HX \qquad (III).$$

The acid employed can be for example: hydrochloric acid, hydrobromic acid, hydriodic acid, sulfuric acid, chloric acid, perchloric acid, thiocyanic acid, nitric acid, phosphoric acid, tetrafluoroboric acid, trichloroacetic acid or trifluoroacetic acid. Preferred as strong acids are perchloric acid, sulfuric acid, hydriodic acid and thiocyanic acid. The acids can be used as such or in the form of their aqueous solutions in the concentration range of 30–100%. The use of aqueous solutions of the acids offers advantages, particularly in connection with the separation of the iminium salts of the formula I from by-products and impurities, and is therefore preferred. The acids are used in at least a stochiometric amount, preferably however in an excess of up to 10 mols per mol of 2-nitrophenyl-N,N-dialkyl-dithiocarbamate of the formula II. The process according to the invention is performed as a rule at temperatures of 0°–200° C., preferably at 20°–100° C. Suitable solvents are in particular dialkyl ketones having 1 to 4 carbon atoms in each of the alkyl groups, and alkyl esters of lower aliphatic carboxylic acids having 2 to 4 carbon atoms in the acid moiety and 1 to 4 carbon atoms in the alcohol moiety. Suitable dialkyl ketones are especially: acetone, methyl ethyl ketone, diethyl ketone and methylisobutyl ketone. Suitable carboxylic acid esters are in particular: ethyl acetate, butyl acetate, ethyl propionate and methyl butyrate.

It is possible by means of anion exchange reactions to replace if desired in a resulting iminium salt of the formula I the acid anion $X^{\ominus}$ present by another preferred acid anion, whereby it can be the anion of a weak acid, for example of a weak organic acid. For this purpose, the iminium salt of the formula I firstly obtained, wherein the anion is for example hydrogen sulfate or chloride, can be reacted in a known manner with a salt of the acid corresponding to the anion desired, for example with an alkali rhodanide. These salts are preferably the corresponding alkali metal or alkaline-earth metal salts. For the anion-exchange reactions, the salts are generally used in a stochiometric excess.

After separation of the solution of the iminium salt of the formula I, the dissolved nitrous acid can be removed in the customary manner by known reactions, such as reaction with amidosulfonic acid, urea or hydroxylamine, by reaction with the solvent (formation of isonitroso compounds) or by reduction, for example with sulfurous acid. The removal of the nitrous acid occurring with the formation of the iminium salts of the formula I can in an advantageous manner be effected also in situ by the iminium salts of the formula I being formed in the presence of a substance which can react with nitrous acid, such as amidosulfonic acid, urea or hydroxylamine, or in the presence of a reducing agent, such as sulfurous acid.

An advantageous embodiment of the process according to the invention comprises converting the 2-nitrophenyl-N,N-dialkyldiethiocarbamate of the formula II, in a reaction medium consisting of water and an organic solvent immiscible with water, in the presence of an acid of the formula III, preferably at a temperature of 0°–100° C., into the corresponding iminium salt of the formula I; separating the organic phase; and obtaining the iminium salts present in aqueous solution, after the addition of fresh organic solvent and neutralisation of the excess acid, in crystalline form.

The 2-nitrophenyl-N,N-dialkyldithiocarbamates of the formula II required as starting materials can be produced in a known manner [cp. J. Org. Chem. 44, (2), 272 (1979)] by reaction of the corresponding 2-nitrochlorophenols with sodium-N,N-dialkyldithiocarbamate.

The action of the compounds according to the invention or of compositions containing them can be considerably broadened and adapted to suit prevailing conditions by the addition of other insecticides and/or acaricides. Suitable additives are for example the following active substances: organic phosphorus compounds, nitrophenols and derivatives thereof, formamidines, ureas, carbamates and chlorinated hydrocarbons.

The compounds of the formula I can be combined with particular advantage also with substances which intensify pesticidal activity. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I can be used on their own or together with suitable carriers and/or additives. Suitable carriers and additives may be solid or liquid and correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art. Also to be mentioned are cattle dips and spray races, in which aqueous preparations are used. These forms of preparation are particularly suitable for combating zooparasitic pests.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

Solid Preparations: dusts, scattering agents or granulates (coated granules, impregnated granules and homogeneous granules);

Liquid Preparations:
(a) water-dispersible concentrates of active substance: wettable powders, pastes and emulsions; and
(b) solutions.

The content of active substance in the described compositions is generally between 0.1 and 95%.

The active substances of the formula I can be formulated for example as follows:

Dusts

The following substances are use to produce (a) a 5% dust and (b) a 2% dust:

(a)

5 parts of active substance,
95 parts of talcum; and (b)

2 parts of active substance,
1 part of highly dispersed silicic acid, and
97 parts of talcum.

The active substance is mixed and ground with the carriers.

Granulate

The following ingredients are used to produce a 5% granulate:

5 parts of active substance,
0.25 part of epoxidised vegetable oil,
0.25 part of cetyl polyglycol ether, 3.50 parts of polyethylene glycol, and
91 parts of kaolin (particle size 0.3–0.8 mm).

The active substance is mixed with the epoxidised vegetable oil and the mixture is dissolved in 6 parts of acetone, and the polyethylene glycol and cetyl polyglycol ether are then added. The solution obtained is sprayed onto kaolin and the acetone is subsequently evaporated off in vacuo.

Wettable Powders

The following constituents are used to produce (a) a 40% wettable powder, (b) and (c) a 25% wettable powder, and (d) a 10% wettable powder:

(a)

40 parts of active substance,
5 parts of sodium lignin sulfonate,
1 part of sodium dibutyl-naphthalene sulfonate, and
54 parts of silicic acid;

(b)

25 parts of active substance,
4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid,
19.5 parts of Champagne chalk, and
28.1 parts of kaolin;

(c)

25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselgur, and
46 parts of kaolin; and (d)

10 parts of active substance,
3 parts of a mixture of the sodium salts of saturated fatty alcohol sulfates,
5 parts of naphthalenesulfonic acid/formaldehyde condensate, and
82 parts of kaolin.

The active substance is intimately mixed in suitable mixers with the additives, and the mixture is then ground in appropriate mills and rollers to thus obtain wettable powders which can be diluted with water to give suspensions of the concentration required.

Emulsifiable Concentrates

The following substances are used to produce (a) a 10% emulsifiable concentrate, (b) a 25% emulsifiable concentrate and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylaralkylsulfonate calcium salt,
40 parts of dimethylformamide, and
43.2 parts of xylene;

(b) 25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene; and (c)

50 parts of active substance,
4.2 parts of tributylphenol-polyglycol ether,
5.8 parts of calcium-dodecylbenzenesulfonate,
20 parts of cyclohexanone, and
20 parts of xylene.

Emulsions of the concentration required can be prepared from these concentrates by dilution with water.

Spray

The following constituents are used to produce (a) a 5% spray and (b) a 95% spray:

(a)

5 parts of active substance,
1 part of epoxidised vegetable oil,
94 parts of ligroin (boiling limits 160°–190° C.);

(b)

95 parts of active substance, and
5 parts of epoxidised vegetable oil.

EXAMPLE 1

Production of 4-n-propylamino-5-nitro-7-trifluoromethyl-1,3-benzodithiol-2-N,N-dimethyliminiumhydrogen sulfate In a reaction flask fitted with stirrer, thermometer and condenser, 350 g (2.5 mols) of 70% sulfuric acid are added portionwise within 30 minutes at 20°–30° C. to a mixture of 206 g (0.5 mol) of 2,4-dinitro-3-n-propylamino-6-trifluoromethylphenyl-N,N-dimethyldithiocarbamate and 450 g of methylisobutyl ketone. The reaction mixture is subsequently heated in the course of 1 hour to 60°–65° C. and then stirred for 4 hours at 60°–65° C. After cooling to room temperature and addition of 90 ml of water, the upper organic phase is separated. To the aqueous phase are added at 0°–5° C. during 1 hour, with stirring, 160 g of 50% sodium hydroxide solution (2.0 mols). The crystals which precipitate are filtered off, washed with a small amount of cold water, and dried in a vacuum drying chamber at 60° C. The title compound having a melting point of 180°–182° C. is thus obtained.

EXAMPLE 2

Production of 4-n-propylamino-5-nitro-7-trifluoromethyl-1,3-benzodithiol-2-N,N-dimethyliminiumperchlorate Into a reaction flask fitted with stirrer, thermometer and reflux condenser are placed 20.6 g (0.05 mol) of 2,4-dinitro-3-n-propylamino-6-trifluoromethyl-N,N-dimethyldithiocarbamate and 2.0 g of methylisobutyl ketone, and there are then added at 60°–65° C., within 30 minutes, 33 g (0.23 mol) of 70% perchloric acid. The reaction medium is subsequently cooled, and at 0°–5° C. are firstly added 20 g of water and afterwards 15.1 g (0.18 mol) of 50% sodium hydroxide solution. The crystals which have precipitated are filtered off, washed with a small amount of cold water, and dried in a vacuum drying chamber at 40° C. to thus obtain the title compound having a melting point of 153°–156° C.

EXAMPLE 3

Production of 4-n-propylamino-5-nitro-7-trifluoromethyl-1,3-benzodithiol-2-N,N-dimethyliminium iodide 11.6 g (0.025 mol) of 4-n-propylamino-5-nitro-7-trifluoromethyl-1,3-benzodithiol-2-N,N-dimethyliminium hydrogen sulfate are dissolved in about 30 ml of water, and 3.9 g (0.026 mol) of sodium iodide in 10 ml of water are added. The product which has precipitated is filtered off, and dried in a vacuum drying chamber. There is thus obtained the title product having a melting point of 188°–190° C.

EXAMPLE 4

Production of 4-n-propylamino-5-nitro-7-trifluoromethyl-1,3-benzodithiol-2-N,N-dimethyliminium rhodanide 4.63 g (0.01 mol) of 4-n-propylamino-5-nitro-7-trifluoromethyl-1,3-benzodithiol-2-N,N-dimethyliminiumhydrogen sulfate, 25 ml of isobutylmethyl ketone and 10 ml of water are placed at room temperature into the reaction vessel. 2.5 g (0.025 mol) of potassium rhodanide, dissolved in 5 ml of water, are quickly added, and the reaction mixture is stirred for 15 minutes at room temperature. The reaction mixture is then extracted with methylene chloride, and the separated organic phase is washed twice with saturated sodium chloride solution, dried over sodium sulfate, and concentrated under reduced pressure. The crude product is recrystallised from acetone/water to yield the title compound having a melting point of 132°–133° C.

The following compounds of the formula I are produced in a manner analogous to that described in the preceding Examples:

EXAMPLE 5

Action against plant-damaging acarides: *Tetranychus urticae* (OP-sensitive) and *Tetranychus cinnabarinus* (OP-tolerant)

The primary leaves of *Phaseolus vulgaris* plants were infested, 16 hours before the test for acaricidal action, with an infested piece of leaf from a mass culture of *Tetranychus urticae* (OP-sensitive) and *Tetranychus cinnabarinus* (OP-tolerant), respectively (tolerance is with respect to compatibility with Diazinon). The infested plants treated in this manner were sprayed dripping wet with test solutions containing 400, 200 and 12.5 ppm, respectively, of the compound to be tested. An assessment was made after 24 hours and again after 7 days, by examination under a binocular microscope, of the living individuals and of the dead individuals. One plant was used per concentration and per test species. During the course of the test, the plants were standing in greenhouse compartments at 25° C.

Compounds according to the Examples 1 to 4 exhibited in this test a good action against *Tetranychus urticae* and *Tetranychus cinnabarinus*. The compound according to Example 4 was effective to the extent of 80–100% with 12.5 ppm against the species of pests examined.

EXAMPLE 6

Plant-miticidal leaf-penetration action on *Tetranychus cinnabarinus* and *Panonychus citri*

Potted bush-bean plants infested with *Tetranychus cinnabarinus*, and potted citrus plants infested with *Panonychus citri*, were used in the test.

The upper side of the leaves of the test plants infested with mites were sprayed with an emulsion preparation containing 800 ppm of the active substance to be tested. After the drying of the sprayed-on coating, the edge of the upper side of a number of infested leaves was bounded with a collar of viscous glue (*Pomono Raupenleim*) in order to prevent any migration of mites from the underside of the upper side to the leaves.

| $R_1$ | $R_2$ | $R_3$ | $R_4$ | $X^{\ominus}$ | Melting point [°C.] |
|---|---|---|---|---|---|
| —CH$_2$—CH$_2$—OCH$_3$ | H | —CH$_3$ | —CH$_3$ | $J^{\ominus}$ | 173–175 |
| —CH(CH$_2$)(CH$_2$) (cyclopropyl) | H | —CH$_3$ | —CH$_3$ | $J^{\ominus}$ | 170–172 |
| —CH$_2$—CH=CH$_2$ | —CH$_2$—CH=CH$_2$ | —CH$_3$ | —CH$_3$ | $J^{\ominus}$ | 144–146 |
| —CH$_2$—CH$_2$—OCH$_3$ | H | —CH$_3$ | —CH$_3$ | SCN$^{\ominus}$ | 119–121 |
| —CH(CH$_2$)(CH$_2$) (cyclopropyl) | H | —CH$_3$ | —CH$_3$ | SCN$^{\ominus}$ | 104–107 |
| —CH$_2$—CH=CH$_2$ | —CH$_2$—CH=CH$_2$ | —CH$_3$ | —CH$_3$ | SCN$^{\ominus}$ | 104–106 |
| —CH$_2$—CH$_2$—CH$_3$ | —CH$_2$—CH$_2$—CH$_3$ | —CH$_3$ | —CH$_3$ | SCN$^{\ominus}$ | 172–174 |
| —CH$_3$ | H | —CH$_3$ | —CH$_3$ | $J^{\ominus}$ | 205–207 |
| —CH$_3$ | H | —CH$_3$ | —CH$_3$ | SCN$^{\ominus}$ | 155–158 |
| —C$_2$H$_5$ | H | —CH$_3$ | —CH$_3$ | $J^{\ominus}$ | 203–205 |
| —C$_2$H$_5$ | H | —CH$_3$ | —CH$_3$ | SCN$^{\ominus}$ | 186–189 |
| —cyclohexyl | H | —CH$_3$ | —CH$_3$ | $J^{\ominus}$ | 202–204 |
| —cyclohexyl | H | —CH$_3$ | —CH$_3$ | SCN$^{\ominus}$ | 171–173 |
| —(CH$_2$)$_4$—CH$_3$ | H | —CH$_3$ | —CH$_3$ | $J^{\ominus}$ | 192–194 |
| —(CH$_2$)$_4$—CH$_3$ | H | —CH$_3$ | —CH$_3$ | SCN$^{\ominus}$ | 119–121 |

The treated plants were then kept in a greenhouse at a temperature of 25° to 29° C. Five days after application of the active substance, the mortality rate of the postembryonal and adult stages was determined in order to establish whether a translaminar action, that is to say, a leaf-penetrating action, of the active substance had occurred.

Compounds according to the preceding Examples 1 to 4 exhibited a good action in the above test. The compound according to Example 4 proved to be 80-100% effective against the tested species of pests.

EXAMPLE 7

Action against zooparasitic mites

Batches consisting of about 50 mites in various stages (larvae, nymphs and imagines) were taken from fowl infested with *Dermanyssus gallinae*. The batches of mites were wetted in each case with the respective aqueous emulsion, suspension or solution of the active substance to be tested in a dilution series. This was effected by pouring the liquid preparation containing the active substance over the respective batch of mites contained in a small test tube; the liquid was subsequently absorbed by means of cotton wool. The mites treated in this manner remained for 72 hours in the test tube. An evaluation was made after this time to determine the minimum concentration of active substance required to effect a 100% mortality rate compared with untreated control batches.

Compounds of the formula I according to the preceding Examples 1 to 4 exhibited a good action in this test.

EXAMPLE 8

Action against Ticks (A) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

An evaluation in the case of the adults was made after 2 weeks and in the case of the larvae after 2 days. There were two repeats for each test.

(B) *Boophilus microplus* (larvae)

With a dilution series analogous to that of Test (A), tests were carried out with 20 sensitive larvae and OP-resistant larvae, respectively, (resistance is with respect to Diazinon compatibility).

Compounds of the formula I according to the Examples 1 to 4 were effective in these tests against adults and larvae of *Rhipicephalus bursa* and against sensitive and OP-resistant larvae, respectively, of *Boophilus microplus*.

EXAMPLE 9

Action against *Musca domestica*

50 g in each case of freshly prepared CSMA nutrient substrate for maggots were weighed off into beakers. A specific amount of a 1% by weight acetonic solution of the respective active substance was transferred by pipette to the nutrient substrate in each beaker. After a thorough mixing up of the substrate, the acetone was allowed to evaporate for at least 20 hours. There were then deposited per active substance and concentration in each case 25 one-day-old maggots of *Musca domestica* in the respective beakers containing the nutrient substrate thus treated. After the maggots had pupated, the formed pupae were separated from the substrate by flushing with water, and placed into vessels closed with perforated lids. The pupae flushed out per batch were counted (toxic effect of the active substance on the development of the pupae). The number of flies which had emerged from the pupae was then determined after 10 days. An evaluation was made on the basis of the minimum effective concentration of the tested compound.

Compounds of the formula I according to Examples 1 to 4 exhibited a good action in the above test.

EXAMPLE 10

Action against *Aedes aegypti*

Specific amounts of a 0.1% acetonic solution of the active substance were transferred by pipette to the surface of 150 ml of water in a container to obtain concentrations of 10, 5 and 1 ppm. After the acetone had evaporated off, 30-40 three-day old Aëdes larvae were placed into each container. The mortality rate was determined after 1, 2 and 5 days.

Compounds of the formula I according to the Examples 1 to 4 exhibited in this test a good action against *Aedes aegypti*.

What is claimed is:

1. The compound of the formula

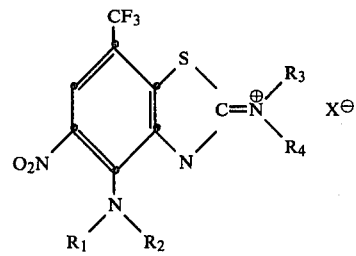

wherein
R$_1$ and R$_2$ independently of one another are each hydrogen, C$_1$-C$_5$-alkyl, C$_3$-C$_6$-cycloalkyl, C$_3$-alkenyl, C$_3$-C$_5$-alkynyl or the radical —(CH$_2$)$_n$—OR, in which R is C$_1$-C$_4$-alkyl, and n is the number 2 or 3, R$_3$ and R$_4$ independently of one another are each C$_1$-C$_4$-alkyl, or together they are the radical —(CH$_2$)$_4$— or —(CH$_2$)$_5$—, and X$^\ominus$ is the molar equivalent of an anion of an inorganic or organic acid.

2. The compound according to claim 1, wherein R$_1$ and R$_2$ independently of one another are each hydrogen, C$_1$-C$_4$-alkyl, C$_3$-C$_6$-cycloalkyl, C$_3$-alkenyl, C$_3$-C$_5$-alkynyl or the radical —(CH$_2$)$_n$—OR, in which R is C$_1$-C$_4$-alkyl, and n is the number 2 or 3.

3. The compound according to claim 2, wherein R$_1$ and R$_2$ independently of one another are each hydrogen, C$_1$-C$_4$-alkyl, C$_3$-alkenyl, C$_3$-alkynyl or 2-methoxyethyl, and R$_3$ and R$_4$ are methyl.

4. The compound according to claim 3, wherein R$_1$ is hydrogen.

5. The compound according to claim 1, wherein X$^\ominus$ is chloride, bromide, iodide, sulfate, hydrogen sulfate, chlorate, perchlorate, rhodanide, nitrate, phosphate, hydrogen phosphate, tetrafluororborate, acetate, chloroacetate, trichloroacetate, trifluoroacetate, phenylsulfonate, oxalate, malonate, succinate, malate, tartrate or citrate.

6. The compound according to claim 5 wherein $X^\ominus$ is perchlorate, hydrogen sulfate, iodide or rhodanide.

7. The compound according to claim 4 of the formula

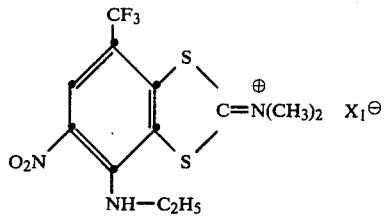

wherein $X_1^\ominus$ is perchlorate, hydrogen sulfate, iodide or rhodanide.

8. The compound according to claim 4 of the formula

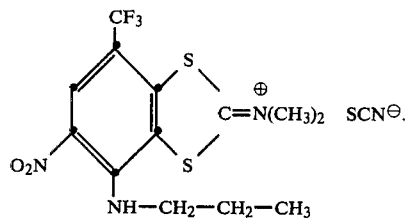

9. A pesticidal composition which comprises as the active ingredient a pesticidally effective amount of a compound according to claim 1 together with suitable carriers and/or other additives or diluents therefor.

10. A method for combating pests, particularly members of the order Acarina, especially mites which damage plants, which method comprises applying to said pests or to a locus desired to be protected from said pests a pesticidally effective amount of a compound according to one of claims 1 to 8.

* * * * *